US011662058B2

United States Patent
MacArthur et al.

(10) Patent No.: US 11,662,058 B2
(45) Date of Patent: May 30, 2023

(54) ORTHOTIC DEVICE FOR USE WITH USER-OPERATED TOOL

(71) Applicant: Honda Motor Co., Ltd., Tokyo (JP)

(72) Inventors: Benjamin MacArthur, Barrie (CA); Angelica Gabrielle Trumpler, Mulmur (CA); Benjamin Douglas DeBoer, Ancaster (CA); Dwayne Switzer, Angus (CA)

(73) Assignee: HONDA MOTOR CO., LTD., Tokyo (JP)

( * ) Notice: Subject to any disclaimer, the term of this patent is extended or adjusted under 35 U.S.C. 154(b) by 427 days.

(21) Appl. No.: 16/662,996

(22) Filed: Oct. 24, 2019

(65) Prior Publication Data

US 2020/0056741 A1 Feb. 20, 2020

Related U.S. Application Data

(63) Continuation-in-part of application No. 15/043,989, filed on Feb. 15, 2016, now Pat. No. 11,389,315.

(51) Int. Cl.
*A61F 5/01* (2006.01)
*F16M 13/04* (2006.01)

(52) U.S. Cl.
CPC ............. *F16M 13/04* (2013.01); *A61F 5/012* (2013.01); *A61F 5/0118* (2013.01)

(58) Field of Classification Search
CPC .......... A61F 5/01; A61F 5/0118; A61F 5/012; A61F 5/05858; A61F 5/05866; A61F 5/05841; A61F 5/05816; A61F 5/013; F16M 13/04; F16M 13/00; B23B 45/003; B23B 45/00; B23B 45/001; B25F 5/00; B25F 5/02; B25F 5/025; B25F 5/021; B25F 5/026; B25F 5/006; B25F 5/003; B25H 1/0021; Y10T 16/4713; B25D 17/043
USPC ............................................ 173/170; 16/426
See application file for complete search history.

(56) References Cited

U.S. PATENT DOCUMENTS

| 2,312,523 | A | * | 3/1943 | Corbett | A61F 5/05866 602/21 |
| 4,413,620 | A | | 11/1983 | Tucker | |
| 5,885,036 | A | * | 3/1999 | Wheeler | B23Q 9/0028 408/1 R |

(Continued)

FOREIGN PATENT DOCUMENTS

| CA | 2285053 A1 | 10/1998 |
| CA | 2321666 A1 | 9/1999 |

OTHER PUBLICATIONS

Dictionary.com, "cast," https://www.dictionary.com/browse/cast.*

(Continued)

*Primary Examiner* — Victoria Hicks Fisher
(74) *Attorney, Agent, or Firm* — Armstrong Teasdale, LLP

(57) ABSTRACT

An orthotic device is coupleable to a fastener installation tool and is configured to be worn on an appendage of a user of the fastener installation tool. The orthotic device is configurable between a relaxed state and a rigid state, and includes at least one activation component responsive to an activation signal output by a controller in communication with the fastener installation tool. The at least one activation component changes the orthotic device from the relaxed state to the rigid state in response to operation of the fastener installation tool.

20 Claims, 5 Drawing Sheets

(56) References Cited

U.S. PATENT DOCUMENTS

| | | | |
|---|---|---|---|
| 6,324,728 B1* | 12/2001 | Blankenheim | B25F 5/021 |
| | | | 16/110.1 |
| 6,540,707 B1 | 4/2003 | Stark et al. | |
| 6,592,538 B1 | 7/2003 | Hotchkiss et al. | |
| 6,969,365 B2 | 11/2005 | Scorvo | |
| 7,513,881 B1* | 4/2009 | Grim | A61F 5/0585 |
| | | | 128/882 |
| 7,641,668 B2* | 1/2010 | Perry | A61M 5/14566 |
| | | | 606/192 |
| 7,740,602 B2 | 6/2010 | Christensen | |
| 8,005,651 B2 | 8/2011 | Summit et al. | |
| 8,613,716 B2 | 12/2013 | Summit et al. | |
| 8,784,350 B2 | 7/2014 | Cohen | |
| 9,931,701 B1* | 4/2018 | Klein | B25F 5/021 |
| 2003/0018286 A1* | 1/2003 | Porrata | A61F 5/0118 |
| | | | 602/21 |
| 2004/0092831 A1 | 5/2004 | Hood, Jr. | |
| 2009/0070938 A1 | 3/2009 | Kell | |
| 2011/0009757 A1 | 1/2011 | Sano et al. | |
| 2011/0054283 A1 | 3/2011 | Shuler | |
| 2012/0037386 A1* | 2/2012 | Cook | B25F 5/021 |
| | | | 173/30 |
| 2012/0101418 A1 | 4/2012 | Manoach et al. | |
| 2013/0023741 A1 | 1/2013 | Ayanruoh | |
| 2014/0070042 A1 | 3/2014 | Beers et al. | |
| 2014/0142485 A1 | 5/2014 | Berry et al. | |
| 2015/0073322 A1 | 3/2015 | Cohen | |
| 2016/0354222 A1* | 12/2016 | Alsolami | A61F 5/012 |

OTHER PUBLICATIONS

DG Industries, "DG Industries Ergonomic Products", http://www.dgindustries.com/Ergonomic_Products.htm, accessed on Dec. 9, 2015.

DG Industries, "Biometric Brace", http://www.dgindustries.com/tour/tour-5.htm, accessed on Dec. 9, 2015.

DG Industries, "SideArm", http://www.dgindustries.com/tour/tour-6.htm, accessed on Dec. 9, 2015.

DG Industries, "Bio-Brace 2.0", http://www.dgindustries.com/tour/tour-4.htm, accessed on Dec. 9, 2015.

DG Industries, "Bio-Brace Classic", http://www.dgindustries.com/tour/tour-1.htm, accessed on Dec. 9, 2015.

Stone, Andy, "Brace Yourself", Forbes, Oct. 26, 2007, 5 pages, http://www.forbes.com/forbes/2007/1112/104.html.

* cited by examiner

ORTHOTIC DEVICE FOR USE WITH USER-OPERATED TOOL

CROSS-REFERENCE TO RELATED APPLICATIONS

This application is a continuation-in-part of U.S. patent application Ser. No. 15/043,989, filed Feb. 15, 2016, the disclosure of which is hereby incorporated by reference in its entirety.

BACKGROUND

The present disclosure relates generally to orthotic devices and, more specifically, to adjustable orthotic devices responsive to operation of a user-operated tool.

When using a hand-operated tool to install fasteners, such as bolts and screws, during the manufacture or maintenance of products, such as automobiles, at least some known tools may accumulate a resistive force (e.g., torque, friction), and impart the resistive force to an operator of the tool. For example, a direct-current (DC) powered tool configured to rotate a fastener at an installation point may accumulate torque generated by the fastener impacting or engaging the installation point. The accumulated resistive force may be at least partially transferred to an operator of the tool.

Repetitive fastener installations and the repetitive transfer of associated forces to the operator of a tool may cause the operator to experience ergonomic fatigue. In particular, the operator may experience ergonomic fatigue due to the repetitive resistive forces absorbed by their arm.

BRIEF SUMMARY

In one aspect, an orthotic device is coupleable to a fastener installation tool and is configured to be worn on an appendage of a user of the fastener installation tool. The orthotic device is configurable between a relaxed state and a rigid state, and includes at least one activation component responsive to an activation signal output by a controller in communication with the fastener installation tool. The at least one activation component changes the orthotic device from the relaxed state to the rigid state in response to operation of the fastener installation tool.

In another aspect, an orthotic system includes a fastener installation tool, a controller coupled in communication with the fastener installation tool and configured to output an activation signal based on operation of the fastener installation tool, and an orthotic device coupled to the fastener installation tool and configured to be worn on an appendage of a user of the fastener installation tool. The orthotic device is configurable between a relaxed state and a rigid state. The orthotic device changes from the relaxed state to the rigid state in response to the activation signal output by the controller.

In yet another aspect, a method includes providing an orthotic device coupled to a fastener installation tool, where the orthotic device is configured to be worn on an appendage of a user of the fastener installation tool. The method further includes outputting, by a controller coupled in communication with the fastener installation tool, an activation signal, based on operation of the fastener installation tool. The method further includes changing the orthotic device from a relaxed state to a rigid state in response to the activation signal output by the controller.

DETAILED DESCRIPTION

The systems and methods described herein relate generally to orthotic devices and, more specifically, to adjustable orthotic devices that are responsive to operation of a user-operated tool.

As described further herein, the orthotic devices of the present disclosure are configured to be coupled to an appendage (e.g., an arm, a hand, a wrist, etc.) of a user operating a tool. Based on operation of the tool, a controller in communication with the tool causes the orthotic device to change from a relaxed state to a rigid state. While in the rigid state, the orthotic device substantially inhibits movement of the appendage coupled to the orthotic device to facilitate preventing resistive forces at the tool from causing injury to the user. Once operation of the tool is completed, the controller causes the orthotic device to change from the rigid state to the relaxed state to permit rotation and movement of the appendage.

Figure 1:
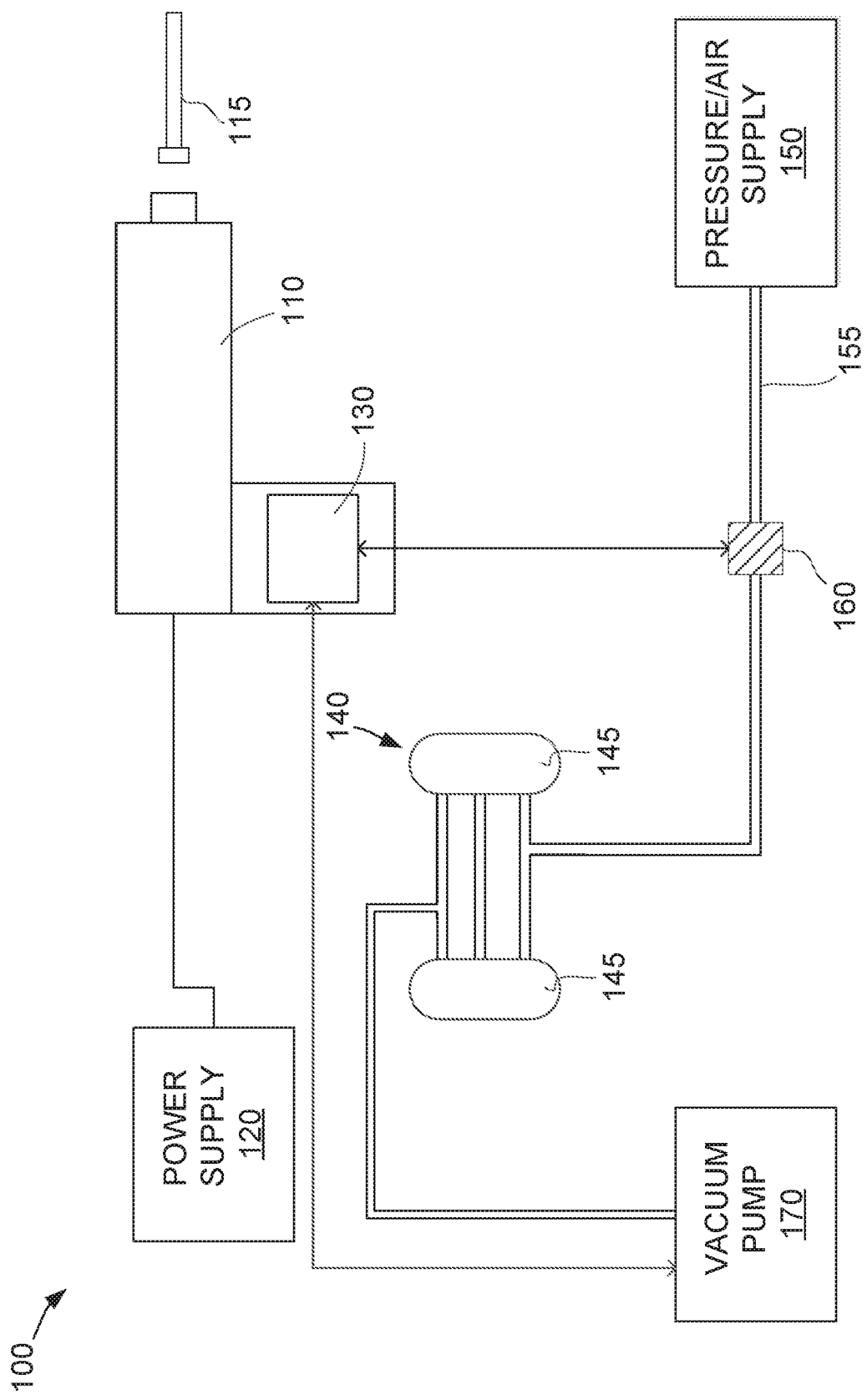
FIG. 1 is a block diagram of an exemplary orthotic system including an adjustable orthotic device.

FIG. 1 is a block diagram of an exemplary orthotic system 100. In the exemplary embodiment, system 100 includes a fastener installation tool 110, a power supply 120, a controller 130, an orthotic device 140, an air supply 150, a valve 160, and a vacuum pump 170. In other embodiments, system 100 may include additional, fewer, or alternative components, including those described elsewhere herein.

In the exemplary embodiment, fastener installation tool 110 is a direct-current (DC) powered tool that generates a reactive force when used to install a fastener, such as a bolt 115. Although fastener installation tool 110 is illustrated as being a right angle installation tool in the exemplary embodiment, fastener installation tool 110 may be any installation tool that enables system 100 to function as described herein. In some embodiments, for example, fastener installation tool 110 may be an in-line fastener installation tool. In other embodiments, fastener installation tool 110 may be a tool other than a DC powered tool, such as an alternating-current (AC) powered tool or a pneumatic tool. In the exemplary embodiment, fastener installation tool 110 is a hand-operated tool. In other embodiments, fastener installation tool 110 may be operated in a different configuration.

Fastener installation tool 110 is configured to install fasteners at installation sites, such as fastener openings defined in automotive frames or panels. In the exemplary embodiment, fastener installation tool 110 is used to install a bolt 115 at an installation site. Although fastener installation tool 110 is described herein with reference to bolt 115, it is understood that fastener installation tool 110 may be configured to install different types of fasteners, including, for example and without limitation, screws, rods, anchors, nails, pins, and the like.

In the exemplary embodiment, fastener installation tool 110 is coupled to power supply 120 to receive power. In the exemplary embodiments, power supply 120 is external to fastener installation tool 110. In other embodiments, power supply 120 may be integrally formed with fastener installation tool 110. In the exemplary embodiment, power supply 120 provides electrical energy to fastener installation tool 110 to generate mechanical energy, such as rotation, to install fasteners. Power supply 120 may be, for example, a DC voltage source, an AC voltage source, a battery, and/or a different component for generating and/or storing electrical energy. Alternatively, power supply 120 may provide a different type of energy. In one embodiment, for example, power supply 120 may be an air compressor or other source of compressed air. Energy provided by power supply 120 is converted to mechanical energy by fastener installation tool (e.g., rotation) to apply a force (e.g., torque) to bolt 115 during installation.

Controller 130 is communicatively coupled to fastener installation tool 110, and transmits and receives control signals to and from system 100 based on one or more operating parameters of fastener installation tool 110, as described in more detail herein. In the exemplary embodiment, controller 130 is integrated within fastener installation tool 110. In other embodiments, controller 130 may be separate from fastener installation tool 110 and may be communicatively coupled to fastener installation tool 110 via any suitable wired and/or wireless communications link.

In some embodiments, controller 130 includes and/or is communicatively coupled to one or more sensors (not shown) that monitor operation of fastener installation tool 110. In some embodiments, fastener installation tool 110 may include the one or more sensors, and may transmit a signal to controller 130 based on data collected by the sensors. In some embodiments, for example, fastener installation tool 110 includes a current sensor (e.g., a current transducer) configured to measure a magnitude of current supplied to fastener installation tool 110. Controller 130 may use the detected current to calculate or estimate the torque applied to bolt 115 and/or the resistive force imparted to fastener installation tool 110 from bolt 115.

Controller 130 may be any suitable controller that enables system 100 to function as described herein, including any suitable analog controller, digital controller, or combination of analog and digital controllers. In some embodiments, controller 130 includes a processor (not shown) that executes instructions for software loaded in a memory device. Controller 130 may generally include any suitable computer and/or other processing unit, including any suitable combination of computers, processing units and/or the like that may be operated independently, or in combination with one another. Thus, in several embodiments, controller 130 may include one or more processor(s) and associated memory device(s) configured to perform a variety of computer-implemented functions including, but not limited to, the functions disclosed herein, such as detecting a resistive force at fastener installation tool 110, outputting an activation signal to one or more components of system 100 in response to a sensed or detected resistive force at fastener installation tool 110, detecting a magnitude of torque applied to a fastener by fastener installation tool 110, and outputting a deactivation signal to one or more components of system 100 when the detected magnitude of torque is equal to a desired installation torque, in accordance with the processes and methods described herein.

As used herein, the term "processor" refers not only to integrated circuits, but also refers to a microcontroller, a microcomputer, a programmable logic controller (PLC), an application specific integrated circuit, and other programmable circuits. Additionally, the memory device(s) of controller 130 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) may generally be configured to store suitable computer-readable instructions that, when implemented by the processor(s), configure and/or cause the associated controller to perform various functions including, but not limited to, the functions described herein.

During installation, in the exemplary embodiment, fastener installation tool 110 applies a torque (i.e., rotational force) or other force to bolt 115 to drive bolt 115 into the installation site. Bolt 115 may produce a reactionary resistive force, such as torque or friction, induced to fastener installation tool 110 during installation of each bolt 115. More specifically, as bolt 115 is rotated, force applied by fastener installation tool 110 and the resistive force produced by bolt 115 may be accumulated at fastener installation tool 110. At least some of the accumulated torque may be transferred to a user of tool 110 during installation.

In the exemplary embodiment, orthotic device 140 is coupled to at least one appendage or joint of the user to which resistive forces from fastener installation tool 110 may be transferred. Orthotic devices described herein are particularly suitable for coupling to the arm, specifically, the forearm, of a user. As used herein, "arm" may refer any portion of the user from the shoulder to the hand of the user. Alternatively, the orthotic devices described herein may be coupled to a different appendage or body part, such as a leg or the torso of the user. Orthotic device 140 is variably positioned between a relaxed state, in which orthotic device 140 permits rotational and lateral movement of the user's appendage or joint, and a rigid state, in which orthotic device 140 is configured to displace or distribute resistive forces from fastener installation tool 110 to facilitate preventing ergonomic fatigue in the appendage or joint coupled to orthotic device 140. In at least some embodiments, orthotic device 140 may be variably positioned to one or more intermediate states defined between the relaxed and rigid states. In the exemplary embodiment, before fastener installation tool 110 is operated, orthotic device 140 is selectively positioned in the relaxed state.

Controller 130 outputs an activation signal based on operation of fastener installation tool 110 that causes orthotic device 140 to change from the relaxed state to the rigid state to enable orthotic device 140 to distribute and/or displace resistive forces imparted to a user's appendage from fastener installation tool 110. In some embodiments, for example, controller 130 senses or detects a resistive force at fastener installation tool 110 during installation of bolt 115. In particular, controller 130 detects a magnitude of an accumulated resistive force and/or a current (i.e., instantaneous) resistive force. In some embodiments, controller 130 calculates or estimates the resistive force based on a magnitude of current supplied to fastener installation tool 110. In response to the detected resistive force, controller 130 may output an activation signal that causes orthotic device 140 to change from the relaxed state to the rigid state to enable orthotic device 140 to distribute and/or displace resistive forces imparted to a user's appendage from fastener installation tool 110. In some embodiments, one or more threshold values may be stored in controller 130 (e.g., stored in one or memory devices of controller 130), and controller 130 may be programmed to compare the detected resistive forces to the one or more threshold values, and to transmit the activation signal when a detected resistive force exceeds one or more threshold values. In certain embodiments, controller 130 may transmit an activation signal to cause orthotic device 140 to change to an intermediate state in response to the detected resistive force.

In yet other embodiments, controller 130 may be configured to output the activation signal based on activation of fastener installation tool 110. That is, controller 130 may sense or detect activation of fastener installation tool 110 (e.g., by detecting that a trigger of fastener installation tool 110 has been depressed or pulled, and/or by initially detecting resistive forces at fastener installation tool 110). In such embodiments, controller 130 may, in response to detecting that fastener installation tool 110 has been activated, output an activation signal that causes orthotic device 140 to change from the relaxed state to the rigid state In some embodiments, controller 130 is further configured to output a deactivation signal that causes orthotic device 140 to change from the rigid state to the relaxed state. In one embodiment, for example, controller 130 outputs a deactivation signal that causes orthotic device 140 to change from the rigid state to the relaxed state when a fastener is installed with a desired installation torque. Controller 130 may detect a final or the last magnitude of torque applied to a fastener by fastener installation tool 110, and output a deactivation signal when the final magnitude of torque is equal to or greater than a desired installation torque. Values for desired installation torques may be stored, for example, in one or more memory devices of controller 130.

Controller 130 may compare the magnitude of the final torque applied to a fastener prior to cessation of a fastener installation process to the desired installation torque to determine if the fastener has been installed at the desired installation torque. For example, when the user stops installing bolt 115, controller 130 detects the magnitude of the last torque applied to bolt 115, and compares that magnitude to the desired installation torque to determine if bolt 115 is installed at the desired installation torque. If the magnitude is equal to or greater than the desired installation torque, controller 130 outputs the deactivation signal to change orthotic device 140 from the rigid state to the relaxed state. If the magnitude is not equal to or greater than the desired installation torque, controller 130 does not output the deactivation signal, and orthotic device 140 is maintained in the rigid state.

In the exemplary embodiment, orthotic device 140 includes one or more bladders 145 (generally, an "activation component") responsive to the activation and deactivation signals output by controller 130. Specifically, in the exemplary embodiment, bladders 145 are selectively inflated and deflated in response to the activation and deactivation signals, respectively, output by controller 130 to modulate orthotic device 140 between the rigid and relaxed states. Bladders 145 receive a fluid, such as air, to cause orthotic device 140 to inflate into the rigid state. As referred to herein with respect to bladders 145, rigid corresponds to inflated and relaxed corresponds to deflated. Controller 130 controls the state of orthotic device 140 by regulating the delivery and removal of fluid to and from bladders 145 of orthotic device 140. Alternatively, orthotic device 140 may be configured to change between the relaxed state and the rigid state using a different configuration. Further, while orthotic device 140 is described with reference to bladders 145 in the exemplary embodiment, orthotic device 140 may include activation components other than bladders, for example, but not limited to, a magnetorheological fluid system, an electrorheological fluid system, and/or any other material or system that allows orthotic device 140 to function as described herein.

In the exemplary embodiment, air supply 150 is coupled in fluid communication with bladders 145 of orthotic device 140 through a fluid conduit 155. Air supply 150 provides fluid, such as air, to bladders 145 of orthotic device 140. Air supply 150 may include, for example and without limitation, a compressed air tank, a pump, or a compressor. In certain embodiments, air supply 150 may be electrically coupled to power supply 120. Air supply 150 may be communicatively coupled to controller 130 to enable controller 130 to selectively adjust one or more operating parameters (e.g., motor speed, voltage, current, etc.) to regulate the supply of air to orthotic device 140. For example, controller 130 may be configured to control the rate of air supplied to bladder 145 such that bladder 145 reaches a pre-determined pressure or inflation amount prior to a desired installation torque being applied to fastener 115. In this way, bladder 145 may reach the desired pressure or inflation amount prior to large resistive forces being imparted to fastener installation tool 110 and a user's arm.

Valve 160 is fluidly coupled between orthotic device 140 and air supply 150, and selectively regulates the supply of air from air supply 150 to orthotic device 140. In one embodiment, valve 160 is integrated with orthotic device 140 and/or is directly coupled to one of bladders 145 (i.e., without an intervening conduit or hose). In another embodiment, valve 160 is integrated with air supply 150. In the exemplary embodiment, valve 160 is an electrically-actuated valve, such as a solenoid valve, and is actuated by control signals transmitted by controller 130. For example, the activation and deactivation signals output by controller 130 cause valve 160 to actuate between an open position and a closed position, respectively. When valve 160 is opened, air from air supply 150 inflates bladders 145 of orthotic device 140. When valve 160 is closed, air flow to bladders 145 from air supply 150 is blocked. In other embodiments, valve 160 may be any suitable type of valve that enables system 100 to function as described herein. By way of example, controller 130 may, in response to detecting that fastener installation tool 110 has been activated, output an activation signal to air supply 150 and/or valve 160 to supply air to bladder 145 such that bladder 145 begins to inflate when fastener installation tool 110 is activated. Alternatively, controller 130 may output an activation signal to air supply 150 and/or valve 160 to supply air to bladder 145 in response to sensing or detecting a resistive force at fastener installation tool 110.

Vacuum pump 170 is coupled in fluid communication with bladders 145 of orthotic device 140 to facilitate removal of air or other fluid from orthotic device 140 to change orthotic device 140 from the rigid state to the relaxed state. In some embodiments, vacuum pump 170 may be coupled to power supply 120. Vacuum pump 170 is communicatively coupled to controller 130 and/or valve 160 to detect a deactivation signal output by controller 130. Vacuum pump 170 is activated in response to receiving the deactivation signal from controller 130 and/or detecting the deactivation signal being output by controller 130. When activated, vacuum pump 170 generates a reduced or negative pressure at one or more outlets of bladders 145 to deflate orthotic device 140 and change orthotic device 140 from the rigid state to the relaxed state. In some embodiments, vacuum pump 170 can deflate orthotic device 140 to an intermediate state. In some embodiments, vacuum pump 170 and air supply 150 may be integrally formed and/or may be fluidly connected as part of a closed fluid circuit. As an alternative to vacuum pump 170, or in combination with vacuum pump 170, system 100 may include a deflation valve configured to allow air to exit bladders 145 when open and to maintain air within bladders 145 when closed.

Figure 2:
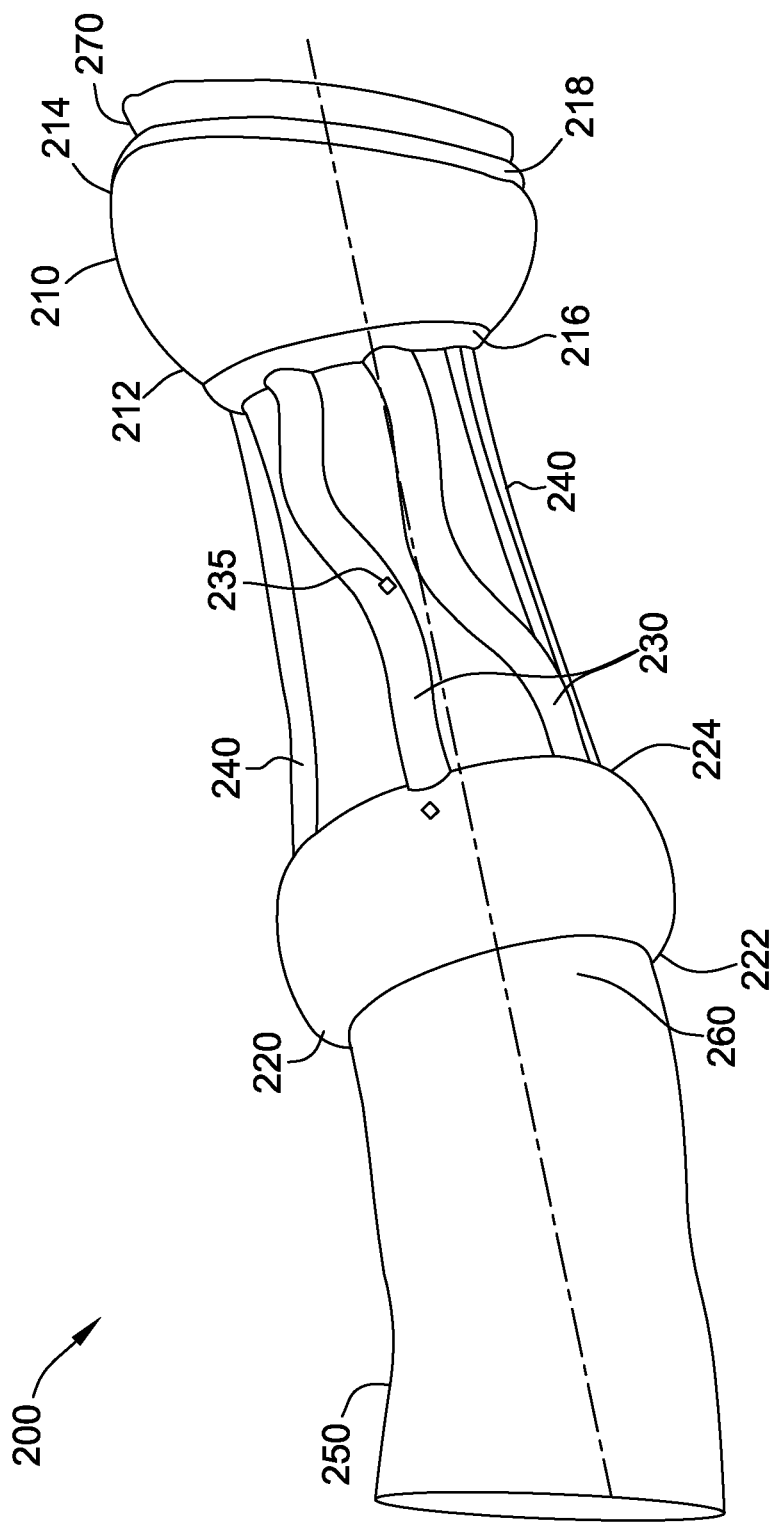
FIG. 2 is a perspective view of an exemplary orthotic device that may be used in the orthotic system shown in FIG. 1.

FIG. 2 is a perspective view of an exemplary orthotic device, shown in the form of an arm brace 200, suitable for use in system 100 (shown in FIG. 1). In the exemplary embodiment, device 200 includes a first bladder 210, a second bladder 220, fluid conduits 230, and braces 240. In other embodiments, device 200 may include additional, fewer, or alternative components or configurations. For example, device 200 may be configured to attach to a different appendage of the user.

In the exemplary embodiment, device 200 couples to an arm 250 of the user. In particular, device 200 is attached to arm 250 when the user is operating a fastener installation tool (e.g., tool 110, shown in FIG. 1) with arm 250. First bladder 210 is configured (e.g., sized and shaped) to be coupled about the wrist of arm 250. Second bladder 220 is configured (e.g., sized and shaped) to be coupled about a forearm 260 of arm 250 and is spaced apart from first bladder 210. In other embodiments, first bladder 210 and second bladder 220 may be positioned and/or coupled at different locations along arm 250. In one embodiment, for example, second bladder 220 is coupled around the elbow of arm 250. Fluid conduits 230 and braces 240 extend between first bladder 210 and second bladder 220, and are circumferentially-spaced about a longitudinal centerline 205 of device 200 to enable device 200 to be inserted onto arm 250.

In the exemplary embodiment, first bladder 210 and second bladder 220 are each an annular or ring-shaped bladder that defines a central opening that is sized and shaped to receive at least a portion of arm 250 therein. First bladder 210 and second bladder 220 are fabricated from a suitably flexible or semi-flexible material (e.g., rubber or plastic) to enable inflation and deflation. In the exemplary embodiment, first bladder 210 includes a first or proximal side 212 sized to fit about the wrist of arm 250, and a second or distal side 214 that is sized to fit about the base of a hand 270 of arm 250. As used herein, "proximal" refers to a direction extending towards the torso of a body (e.g., towards a shoulder of arm 250) and "distal" refers to a direction extending away from the torso of the body (e.g., towards hand 270). The opening defined by first bladder 210 is smaller at proximal side 212 than at distal side 214 to facilitate securely fitting around the wrist of arm 250 and the base of hand 270. In the exemplary embodiment, the opening defined by second bladder 220 has a substantially constant diameter, although in other embodiments, the opening defined by second bladder 220 may be tapered from a proximal side 222 of second bladder 220 to a distal side 224 of second bladder 220.

In the exemplary embodiment, device 200 includes a first support ring 216 and a second support ring 218. First support ring 216 is coupled to proximal side 212 of first bladder 210 and second support ring 218 is coupled to distal side 214 of first bladder 210. First support ring 216 and second support ring 218 are constructed from a rigid or semi-rigid material and are sized and shaped to fit arm 250. In some embodiments, first support ring 216 and second support ring 218 are formed integrally with first bladder 210 (e.g., by an additive manufacturing process). When first bladder is inflated, first bladder 210 biases second support ring 218 away from first support ring 216 and into engagement with the base of hand 270 to substantially inhibit rotation of hand 270 relative to forearm 260.

Fluid conduits 230 extending from first bladder 210 to second bladder 220 are circumferentially-spaced around longitudinal centerline 205. When device 200 is coupled to arm 250, fluid conduits 230 are circumferentially-spaced around arm 250 as well. Fluid conduits 230 are constructed from rigid or semi-rigid materials, and may facilitate limiting rotation of first bladder 210 relative to second bladder 220. Fluid conduits 230 fluidly couple first bladder 210 and second bladder 220 such that inflating either of first bladder 210 or second bladder 220 causes the other of first bladder 210 and second bladder 220 to inflate. Similarly, deflating either of first bladder 210 or second bladder 220 causes the other of first bladder 210 and second bladder 220 to deflate. In other embodiments, fluid conduits 230 may permit inflation and/or deflation of first bladder 210 and second bladder 220 asymmetrically and/or asynchronously. In one embodiment, for example, fluid conduits 230 are configured such that first bladder 210 deflates only after second bladder 220 has deflated. Although two fluid conduits 230 are illustrated in the exemplary embodiment, device 200 may include any number of fluid conduits 230 that enables device 200 and/or system 100 to function as described herein. In some embodiments, for example, device 200 may include a single (i.e., only one) fluid conduit 230.

Braces 240 extend from first bladder 210 to second bladder 220, and are circumferentially-spaced around longitudinal centerline 205. Braces 240 are constructed from suitably rigid materials and provide a relatively rigid mechanical link between first bladder 210 and second bladder 220 such that braces 240 transmit rotational forces (e.g., rotational forces imparted to hand 270 from a fastener installation tool) from first bladder 210 to second bladder 220. The exemplary embodiment includes two braces 240 coupled to diametrically-opposed sides of device 200. In other embodiments, device may include more or less than two braces. In some embodiments (e.g., where a joint of arm 250 is between first bladder 210 and second bladder 220), fluid conduits 230 and/or braces 240 may be hinged to permit movement of a joint of arm 250.

Device 200 includes one or more fluid inlet and outlet ports for coupling to a fluid supply and/or a pump (e.g., air supply 150 and vacuum pump 170, shown in FIG. 1) for inflating and deflating first bladder 210 and second bladder 220. In the exemplary embodiment, a single fluid port, shown in the form of an opening 235, is formed on one of fluid conduits 230, though fluid ports may be located along any other portion of device 200 that enables fluid flow into and/or out of first bladder 210 and/or second bladder 220. In some embodiments, first bladder 210 includes either a fluid inlet port or a fluid outlet port, and second bladder includes the other of a fluid inlet port or a fluid outlet port. In other embodiments, one fluid conduit 230 includes a fluid inlet port, and another of fluid conduit 230 includes a fluid outlet port. In yet other embodiments, at least one fluid port is formed on either first support ring 216 and/or second support ring 218. The fluid ports include a suitable coupling structure to permit coupling to fluid conduits, such as fluid conduit 155 (shown in FIG. 1). In some embodiments, device 200 may include a single fluid port that acts as both a fluid inlet and a fluid outlet. In yet other embodiments, device 200 includes separate fluid inlet and outlet ports.

When device 200 is in the relaxed state (i.e., when first bladder 210 and second bladder 220 are deflated), device 200 permits unrestricted movement and rotation of arm 250, forearm 260, and hand 270. When device 200 is in the rigid state (i.e., when first bladder 210 and second bladder 220 are inflated, shown in FIG. 2), device 200 restricts movement and rotation of arm 250, and more specifically, relative movement and rotation of forearm 260 and hand 270. In particular, first bladder 210 and second bladder 220 restrict movement of the wrist of arm 250 and hand 270 to prevent injuries from resistive forces at the fastener installation tool. Resistive forces may cause the wrist and/or hand 270 to rotate, bend, or otherwise move in a manner that may induce or cause injury to a user. By inflating and restricting joint movement, first bladder 210 and second bladder 220 may facilitate reduced movement of arm 250 from resistive forces and reduced injuries associated with the resistive forces. In addition to restricting movement of arm 250, device 200 distributes or displaces the resistive forces and rotational forces at, for example, the wrist or hand to device 200 and/or another portion of arm 250, such as forearm 260. Distributing the resistive forces facilitates reduced stress or strain at a particular portion of arm 250.

More specifically, when first bladder 210 is inflated, first support ring 216 and second support ring 218 are biased away from one another and into engagement the wrist and hand 270, respectively, thereby inhibiting bending of hand 270 about the wrist. Moreover, when second bladder 220 is inflated, rotation of device 200 relative to arm 250 is inhibited such that rotational forces imparted on hand 270 from an external source (e.g., fastener installation tool 110) are transmitted and distributed across a larger and more massive portion of arm 250, such as forearm 260. More specifically, rotational forces imparted to hand 270 from a fastener installation tool are transferred to device 200 at first bladder 210, which are transmitted to second bladder 220 through braces 240. Such rotational forces are imparted to arm 250 through second bladder 220 because rotation of device 200 relative to arm 250 is substantially inhibited when device 200 is in the rigid state (i.e., when first bladder 210 and second bladder 220 are inflated). Device 200 thereby transmits and distributes rotational forces imparted on hand 270 across a larger and more massive portion of arm 250 to facilitate injury prevention and reducing user fatigue.

In the exemplary embodiment, device 200 is custom fitted to arm 250 to facilitate secure coupling between device 200 and arm 250. Any suitable method may be employed to custom fit device 200 to a user. In one embodiment, for example, the user's arm 250 is scanned (e.g., with a 3-D imaging system) and, based on the scan and/or other measurements of arm 250, components of device 200 are suitably sized and shaped to fit securely around arm 250. In at least some embodiments, one or more components of device 200 are fabricated using additive manufacturing techniques (also referred to as three-dimensional (3D) printing). In some embodiments, device 200 may be unitarily formed using additive manufacturing techniques to facilitate on-demand production for new users and reduce assembly time and costs.

Figure 3:
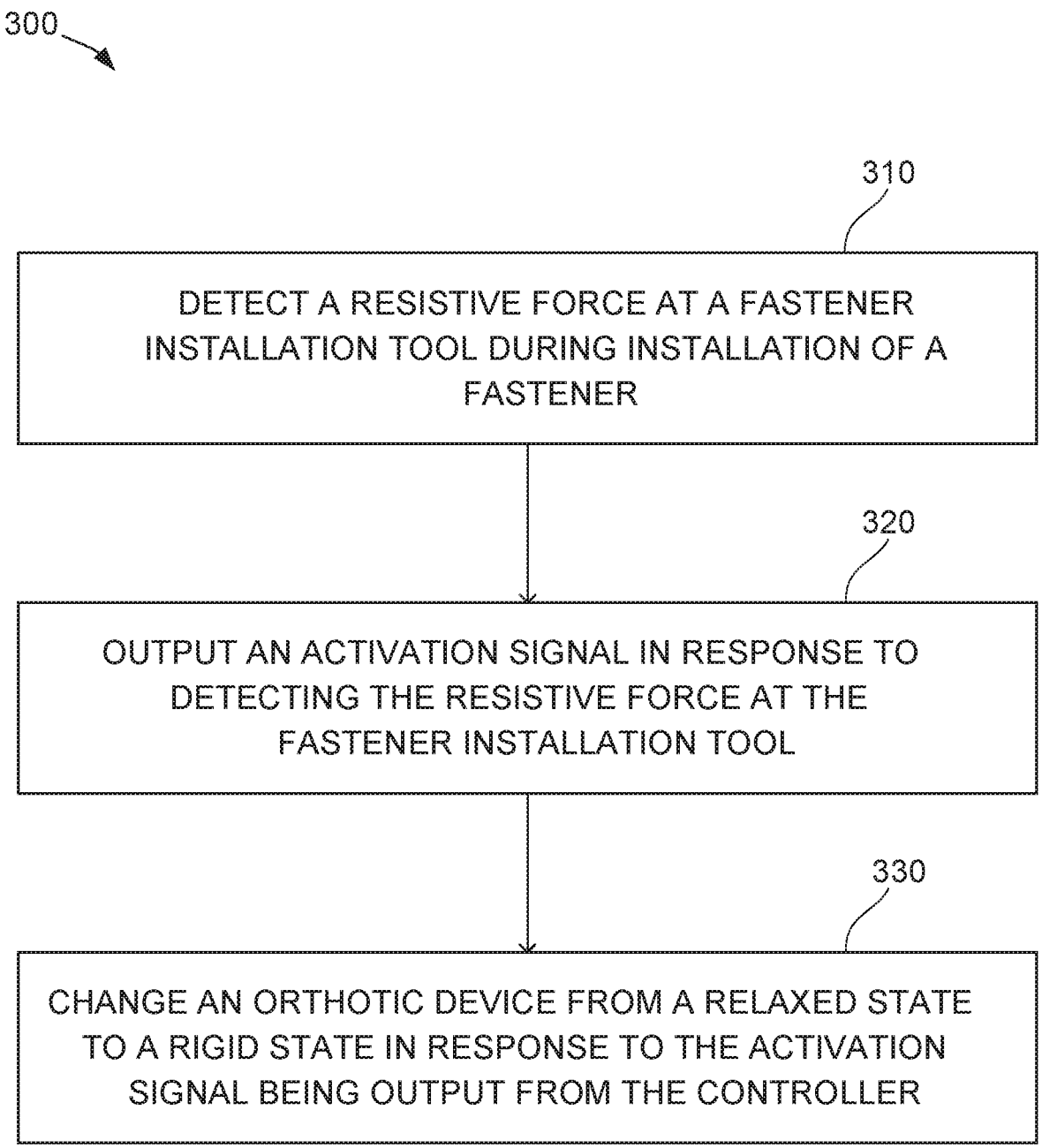
FIG. 3 is a flow diagram of an exemplary method of operating an orthotic device in the orthotic system shown in FIG. 1.

FIG. 3 is a flow diagram of an exemplary method 300 of operating an orthotic system (e.g., system 100, shown in FIG. 1) including a fastener installation tool, a controller coupled to the fastener installation tool, and an orthotic device configured to be worn on an arm of a user of the fastener installation tool. In other embodiments, method 300 includes additional, fewer, or alternative steps, including those described elsewhere herein.

Method 300 begins with the controller detecting 310 a resistive force at the fastener installation tool during installation of a fastener. In some embodiments, the controller detects 310 a resistive force that exceeds a threshold value. The controller outputs 320 an activation signal in response to detecting the resistive force at the fastener installation tool. In the exemplary embodiment, the activation signal is received by a valve coupled between a fluid supply and the orthotic device that opens and closes in response to control signals from the controller. In response to the activation signal being output from the controller, the orthotic device changes 330 from a relaxed state to a rigid state to restrict rotational movement of the arm and to distribute forces imparted to the arm of a user from the fastener installation tool. In at least some embodiments, the orthotic device includes at least one bladder. In, such embodiments, changing 330 the orthotic device from the relaxed state to the rigid state includes inflating the bladder by opening the valve to permit fluid flow from the fluid supply into the bladder. In the exemplary embodiment, when the controller detects that a fastener is installed with a desired installation torque, the controller outputs a deactivation signal that causes the orthotic device to change from the rigid state to the relaxed state. Specifically, in the exemplary embodiment, the controller outputs a deactivation signal that closes the valve to stop the flow of fluid to the at least one bladder, and activates a vacuum pump to facilitate removal of fluid from the at least one bladder.

Figure 4:
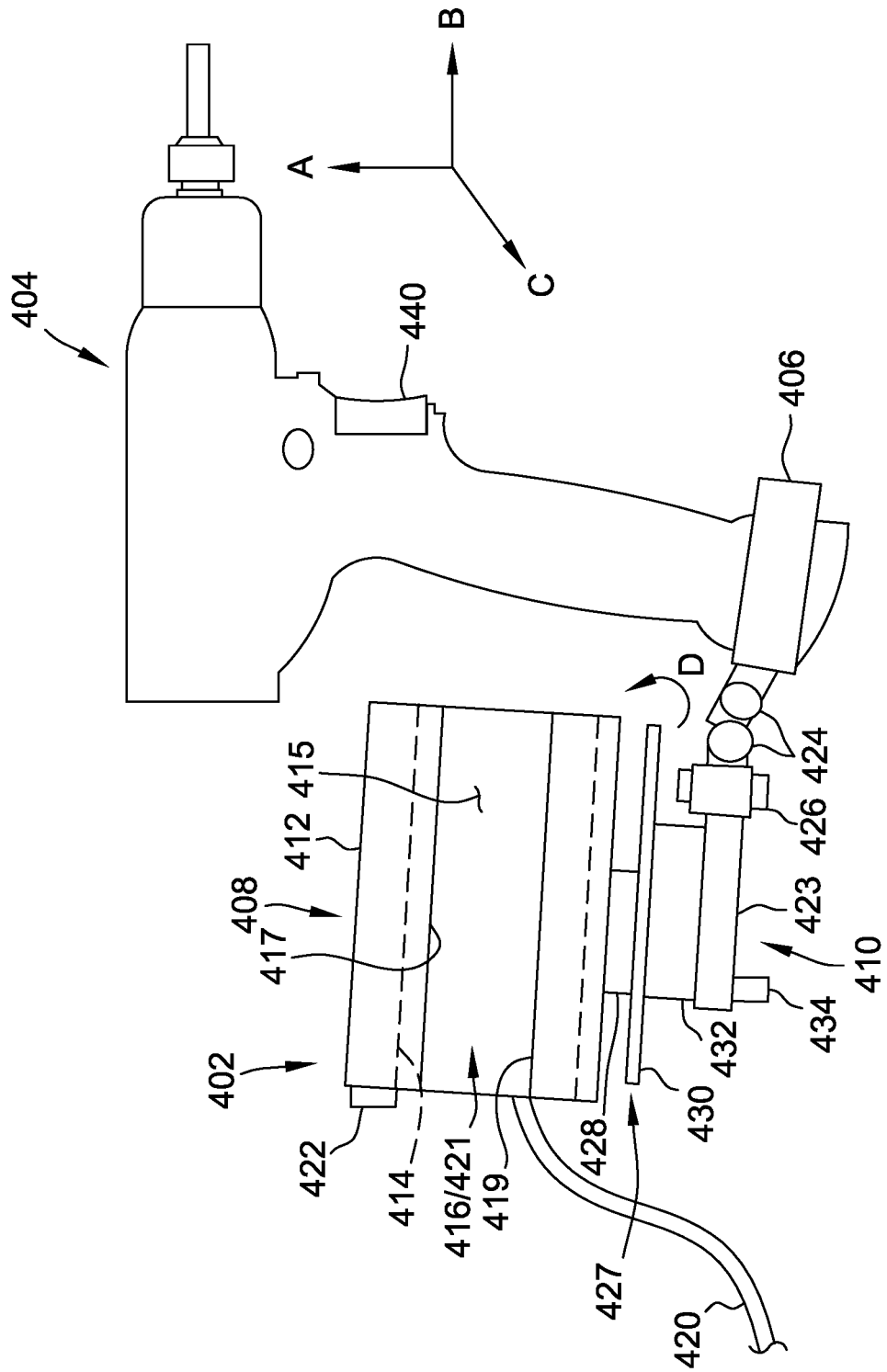
FIG. 4 is a schematic view of a second exemplary orthotic device that may be used in the orthotic system shown in FIG. 1.

FIG. 4 is a schematic view of another embodiment of an orthotic device, shown in the form of an arm brace 402, suitable for use in system 100 (shown in FIG. 1). In this embodiment, orthotic device 402 is coupled to a fastener installation tool 404, which may have the same configuration and operate in the same manner as fastener installation tool 110 described with reference to FIG. 1. Orthotic device 402 may be removably coupled to fastener installation tool 404 by a suitable coupler, such as a clamp 406. Clamp 406 is sized and shaped to removably couple to fastener installation tool 404, and may generally include any suitable clamp known in the art, including clamps with semi-circular locking jaws. In other embodiments, orthotic device 402 or a portion thereof may be permanently fixed to fastener installation tool 404. Rigidly coupling orthotic device 402 to fastener installation tool 404 prevents rotation of a user's wrist with respect to fastener installation tool 404.

In the exemplary embodiment, orthotic device 402 includes clamp 406, an appendage housing 408, and a base or main body 410 coupled to clamp 406. Appendage housing 408 is configured (e.g., sized and shaped) to receive and support an appendage of a user of fastener installation tool 404. In the exemplary embodiment, appendage housing 408 is sized and shaped to support an arm of the user, specifically a forearm of the user. In other embodiments, appendage housing 408 may receive any portion of the arm of the user including, for example, a wrist of the user. In yet other embodiments, appendage housing 408 may receive an appendage other than an arm of the user.

Appendage housing 408 includes a cuff or shell 412 and a bladder 414 (generally, an "activation component"). Bladder 414 is fabricated from any suitably flexible or semi-flexible material (e.g., rubber or plastic) to enable inflation and deflation. In the exemplary embodiment, shell 412 is fabricated from a more rigid material than bladder 414 (e.g., plastic, metal, composite, etc.), and is configured to surround and protect bladder 414 (e.g., from punctures).

Shell 412 extends around and partially defines an interior space 415 that is sized and shaped to receive a user's appendage therein. Interior space 415 is formed as an elongate passage that extends axially through appendage housing 408 in the embodiment illustrated in FIG. 4, although interior space 415 may have any other suitable configuration that enables orthotic device to function as described herein. Shell 412 is "C"-shaped in the exemplary embodiment, and includes first and second free ends or edges 417, 419 that define an opening 416 that provides access to interior space 415 such that a user may slide or insert their appendage (e.g., arm) into interior space 415 of shell 412.

Bladder 414 is coupled to shell 412, and generally conforms to the shape of shell 412. Bladder 414 is positioned within interior space 415 enclosed by shell 412, and engages an interior surface of shell 412. When orthotic device 402 is worn on a user's appendage, bladder 414 is disposed between the user's appendage and shell 412. In the exemplary embodiment, bladder 414 is "C"-shaped, and defines an opening 421 aligned with opening 416 defined by shell 412 to allow a user to insert their appendage into interior space 415.

Bladder 414 is coupled in fluid communication with an air supply (e.g., air supply 150, shown in FIG. 1) by a fluid conduit 420 (e.g., substantially similar to fluid conduit 155 shown in FIG. 1) to receive air or other fluid to inflate bladder 414 and change orthotic device 402 from a relaxed state to a rigid state. Bladder 414 also includes an exhaust port 422 through which fluid is expelled from bladder 414. In some embodiments, exhaust port 422 is coupled to a vacuum pump (e.g., vacuum pump 170) by a fluid conduit (not shown in FIG. 4) to facilitate removal of air or other fluid from orthotic device 140 to change orthotic device 140 from the rigid state to the relaxed state. Additionally or alternatively, exhaust port 422 may include an electrically-actuated valve that is activated by a controller (e.g., controller 130) to release fluid from within bladder 414.

Main body 410 is coupled to and provides structural support for appendage housing 408. In the exemplary embodiment, main body 410 is mechanically coupled or linked between clamp 406 and appendage housing 408. Main body 410 is pivotably coupled to clamp 406 in the exemplary embodiment to allow main body 410 and appendage housing 408 to pivot or rotate relative to fastener installation tool 404.

In the exemplary embodiment, main body 410 includes a base plate 423. Base plate 423 is constructed of a suitably rigid material, such as plastic, metal, ceramics, and combinations thereof. Base plate 423 is pivotably coupled to clamp 406. In the exemplary embodiment, base plate 423 is pivotably coupled to clamp 406 by at least one horizontal dowel or pivot pin 424. One pivot pin 424 allows main body 410 to rotate about a horizontal axis with respect to fastener installation tool 404. Multiple pivot pins 424 allow pivoting or rotation of main body 410 about horizontal axes (i.e., axes parallel to axis "C" in FIG. 4) such that orthotic device 402 can pivot upward and downward movement (e.g., in direction of axis "A" in FIG. 4) relative to fastener installation tool 404. In other embodiments, main body 410 may include fewer or more pivot pins 424 to allow for different magnitudes of upward and downward movement. Main body 410 is also coupled to clamp 406 by a vertical pivot pin 426. Pivot pin 426 allows pivoting or rotation of main body 410 about a vertical axis (i.e., an axis parallel to axis "A") such that the orthotic device 402 can pivot leftward and rightward (e.g., in direction of axis "C") relative to fastener installation tool 404.

In the exemplary embodiment, orthotic device 402 also includes a linear slide 427 and a swivel 432 that allows appendage housing 408 to be selectively adjusted to accommodate left-handed and right-handed users, and users with different sized appendages (e.g., arms). In particular, appendage housing 408 is operatively coupled to base plate 423 by linear slide 427 and swivel 432 such that the position and orientation of appendage housing 408 can be selectively adjusted relative to base plate 423 using linear slide 427 and swivel 432. Linear slide 427 allows appendage housing 408 to be moved linearly towards and away from fastener installation tool 404 such that the distance between appendage housing 408 and fastener installation tool 404 can be selectively adjusted to accommodate different sized arms. Swivel 432 allows appendage housing 408 to be rotated (e.g., approximately 180°) such that opening 416 defined by shell 412 can be selectively adjusted to be rightward facing or leftward facing (relative to fastener installation tool 404).

In the exemplary embodiment, linear slide 427 includes a rail 430 and a linear bearing 428 slideably coupled to rail 430. Linear bearing 428 is coupled to shell 412 such that appendage housing 408 can be moved toward or away from (e.g., parallel to axis B) fastener installation tool 404. For example, if a user has a shorter arm, linear bearing 428 is moved along rail 430 toward fastener installation tool 404 such that the distance between appendage housing 408 and fastener installation tool 404 is reduced. On the other hand, if a user has a longer arm, linear bearing 428 is moved along rail 430 away from fastener installation tool 404 such that the distance between appendage housing 408 and fastener installation tool 404 is increased.

In the exemplary embodiment, swivel 432 is a vertical swivel. That is, swivel 432 is configured to allow appendage housing 408 to rotate about a vertical axis (i.e., an axis parallel to axis A) in the direction indicated by arrow "D". In other embodiments, swivel 432 may be other than a vertical swivel, such as a horizontal swivel that permits appendage housing 408 to rotate about a horizontal axis (e.g., an axis parallel to axis B). Further, in the exemplary embodiment, swivel 432 is coupled between linear slide 427 and base plate 423 such that both linear slide 427 and appendage housing 408 rotate about the rotational axis of swivel 432. In other embodiments, swivel 432 may be coupled to base plate 423 or another component of orthotic device 402 such that only appendage housing 408 is rotatable by swivel 432. That is, in other embodiments, linear slide 427 may not be rotatable by swivel 432. A swivel lock or latch 434 is operatively coupled to swivel 432, is selectively positionable between a locked position, in which rotation of swivel 432 is inhibited, and an unlocked position, in which rotation of swivel 432 is permitted. In the exemplary embodiment, swivel lock 434 is coupled to plate 423, though swivel lock 434 may be coupled to any other suitable portion of orthotic device 402 that enables orthotic device 402 to function as described herein.

Swivel 432 allows orthotic device 402 to be selectively configured between a left-handed configuration and a right handed configuration such that orthotic device 402 can used by both left-handed and right-handed users. For example, if a user has a dominant left hand, the user can rotate orthotic device 402 using swivel 432 in direction D from the right-handed configuration (e.g., shown in FIG. 4) to the left-handed configuration, in which opening 416 is leftward facing.

In operation, orthotic device 402 may be implemented in a system with fastener installation tools (e.g., a vehicle assembly line), such as system 100, and operate in substantially the same manner as orthotic device 140 described above with reference to FIG. 1. For example, when orthotic device 402 is in the desired configuration for the user (e.g., when linear bearing 428 is in a position along rail 430 that fits the arm length of the user, and when swivel 432 is in the desired configuration), the user may position their arm in orthotic device 402 (e.g., through opening 416 when orthotic device 402 is in a relaxed state) such that orthotic device 402 is coupled to the user's arm. The user may then grasp fastener installation tool 404 to install one or more fasteners (e.g., bolts 115). The user can also easily remove their arm from orthotic device 402 when they are finished using fastener installation tool 404.

A controller (e.g., controller 130) outputs an activation signal to air supply 150 and/or valve 160 to inflate bladder 414 and change orthotic device 402 from the relaxed state to the rigid state based on operation of fastener installation tool 404. In some embodiments, for example, controller 130 outputs the activation signal in response to fastener installation tool 404 being activated (e.g., by a user pulling or depressing a trigger 440 of fastener installation tool 404). That is, as soon as controller 130 senses that trigger 440 has been pressed (e.g., through a sensor incorporated in trigger 440, not specifically shown), controller 130 outputs an activation signal to air supply 150 and/or valve 160 to supply pressure or air to bladder 414 such that bladder 414 inflates. In other embodiments, controller 130 may output an activation signal to air supply 150 and/or valve 160 to inflate bladder 414 based on other operation of fastener installation tool 404, such as when a certain amount of resistive force is detected at fastener installation tool 404 as described herein. Controller 130 may be configured to control the rate of air supplied to bladder 145 such that bladder 145 reaches a pre-determined pressure or inflation amount prior to a desired installation torque being applied to fastener 115. In this way, bladder 145 may reach the desired pressure or inflation amount prior to large resistive forces being imparted to fastener installation tool 110 and a user's arm.

Controller 130 outputs a deactivation signal (e.g., to vacuum pump 170 and/or a valve of exhaust port 422) to change orthotic device 402 from the rigid state to the relaxed state. In some embodiments, for example, controller 130 outputs a deactivation signal in response to detecting that a fastener (e.g., bolt 115) is installed with a desired installation torque, as described elsewhere herein. In one particular embodiment, for example, controller 130 outputs a deactivation signal to exhaust port 422 such that exhaust port 422 opens and air within bladder 414 is expelled through exhaust port 422. Additionally or alternatively, controller 130 may output deactivation signal to vacuum pump 170 to activate vacuum pump 170 to facilitate deflating bladder 414. The user may repeat the fastener installation process as desired, and remove the orthotic device 402 from their arm when the orthotic device 402 is in the relaxed state (i.e., when bladder 414 is deflated).

Figure 5:
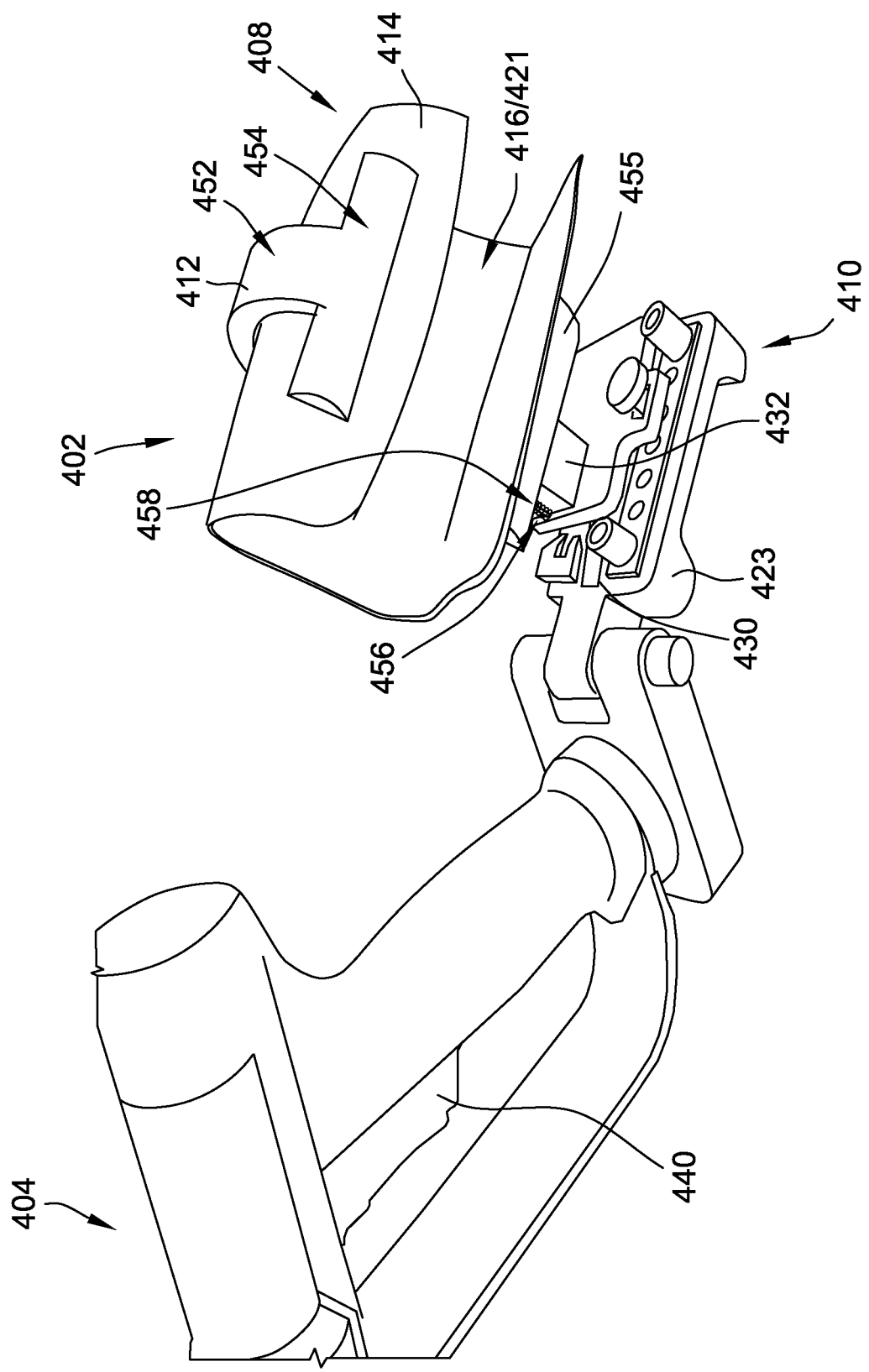
FIG. 5 is a perspective view of the orthotic device shown in FIG. 4 shown in an alternative configuration.

FIG. 5 is a perspective view of orthotic device 402 illustrating details of an alternative shell 412 and swivel 432. Specifically, shell 412 includes a first, C-shaped portion 452 that extends partially circumferentially around bladder 414, and second and third portions 454, 455 coupled to and oriented perpendicular to first portion 452. First portion 452 has a width less than a length of bladder 414 such that bladder 414 extends longitudinally beyond axially ends of first portion 452. Second and third portions 454, 455 define opening 416, and are located on opposite sides of opening 416. In the embodiment illustrated in FIG. 5, swivel 432 includes a spring 456 and a pin 458. Pin 458 extends vertically from swivel 432 through base plate 423 to the swivel lock or latch (not labeled in FIG. 5) located on a bottom of base plate 423. Spring 456 is disposed between a head of pin 458 and swivel 432 such that spring 456 biases swivel 432 towards base plate 423. When the swivel lock is in the unlocked position, pin 458 is raised, allowing swivel 432 to be raised against biasing force of spring 456, and rotate to position appendage housing 408 in the desired configuration. When the swivel lock is in the locked position, the head of pin 458 is pulled down against spring 456, applying a greater biasing force on swivel 432 and restricting movement of swivel 432. In this embodiment, swivel lock can include, for example and without limitation, an over-center latch.

The systems and methods described herein facilitate preventing injuries and reducing fatigue of operators operating tools, such as fastener installation tools. In particular, embodiments of the orthotic systems and methods described herein include an orthotic device that is switched between relaxed and rigid states based on operation of the fastener installation tool. The orthotic device is configured to permit free movement of an appendage in the relaxed state, and to restrict movement of the appendage in the rigid state to prevent injuries and reduce fatigue. The orthotic device is configured to provide these benefits without increasing process time by ensuring that the user can position their arm within the orthotic device and remove their arm from the orthotic device in substantially the same amount of time needed to pick up or set down the fastener installation tool. The orthotic device is activated based on operation of a fastener activation tool, such as upon initial activation of the tool or upon resistive forces being detected at the fastener installation tool. Activating the orthotic device based on operation of the fastener installation tool provides an improvement over other orthotic devices that rely on detection of user movement to modify a state of the orthotic device. In particular, activating the orthotic device based on initial activation of the tool or on detected resistive forces at the fastener installation tool provides more responsive and faster acting orthotic devices as compared to devices that rely on detected user movement resulting from resistive forces being imparted to the user's arm. Embodiments of the systems and method described herein thereby facilitate reducing ergonomic fatigue. In addition, manufacturing customized orthotic devices for each user with additive manufacturing techniques facilitates comfortable and correct fitting for a user and on-demand production of the orthotic device.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An orthotic device coupleable to a fastener installation tool and configured to be worn on an appendage of a user of the fastener installation tool, said orthotic device configurable between a relaxed state and a rigid state, said orthotic device comprising:
   a base; and
   an appendage housing coupled to said base, said appendage housing comprising at least one activation component responsive to an activation signal output by a controller in communication with the fastener installation tool, wherein said at least one activation component changes said orthotic device from the relaxed state to the rigid state in response to operation of the fastener installation tool, and wherein said base is pivotably couplable to a handle of the fastener installation tool.

2. The orthotic device of claim 1, wherein said orthotic device is removeably coupleable to the fastener installation tool.

3. The orthotic device of claim 1 further comprising a clamp sized and shaped to removably couple said base to the handle of the fastener installation tool.

4. The orthotic device of claim 1, wherein the controller outputs the activation signal in response to detecting activation of the fastener installation tool.

5. The orthotic device of claim 1, wherein said appendage housing comprises a shell partially enclosing an interior space, wherein said at least one activation component is coupled to said shell and positioned within the interior space.

6. The orthotic device of claim 5, wherein said at least one activation component comprises at least one bladder configured to be worn around the appendage of the user of the fastener installation tool, wherein the controller outputs the activation signal in response to detecting activation of the fastener installation tool and said at least one bladder is inflated in response to the activation signal output by the controller.

7. The orthotic device of claim 5, wherein said shell defines an opening that provides access to the interior space, wherein the opening is sized and shaped to receive the appendage of the user of the fastener installation tool.

8. The orthotic device of claim 5, wherein said shell is C-shaped.

9. The orthotic device of claim 5 wherein the base includes a base plate and a swivel, wherein said shell is operatively coupled to said base plate by said swivel such that said shell is positionable between a right-handed configuration and a left-handed configuration.

10. The orthotic device of claim 5 further comprising a linear slide coupled to said shell such that said shell is adjustable to accommodate different sized appendages.

11. The orthotic device of claim 1, wherein said orthotic device is selectively configurable between a left-handed configuration and a right-handed configuration.

12. An orthotic system comprising:
a fastener installation tool;
a controller coupled in communication with said fastener installation tool and configured to output an activation signal based on operation of said fastener installation tool; and
an orthotic device coupled to said fastener installation tool and configured to be worn on an appendage of a user of said fastener installation tool, said orthotic device configurable between a relaxed state and a rigid state, wherein said orthotic device changes from the relaxed state to the rigid state in response to the activation signal output by said controller, said orthotic device comprising a base and an appendage housing coupled to said base, said appendage housing comprising at least one activation component responsive to the activation signal output by said controller, wherein said at least one activation component changes said orthotic device from the relaxed state to the rigid state in response to the activation signal, and wherein said base is pivotably coupled to a handle of said fastener installation tool.

13. The orthotic system of claim 12, wherein said orthotic device is removeably coupled to said fastener installation tool.

14. The orthotic system of claim 12, wherein said controller outputs the activation signal in response to detecting activation of said fastener installation tool.

15. The orthotic system of claim 12, wherein said at least one activation component comprises at least one bladder configured to be worn around the appendage of the user of said fastener installation tool, wherein said at least one bladder is inflated in response to the activation signal output from said controller.

16. The orthotic system of claim 15 further comprising:
an air supply; and
an electrically-actuated valve coupled between said air supply and said at least one bladder and configured to control supply of air into said at least one bladder, wherein said electrically-actuated valve is communicatively coupled to said controller and configured to open in response to receiving the activation signal from said controller.

17. The orthotic system of claim 12, wherein said orthotic device is selectively configurable between a left-handed configuration and a right-handed configuration.

18. A method comprising:
providing an orthotic device coupled to a fastener installation tool, the orthotic device configured to be worn on an appendage of a user of the fastener installation tool and configurable between a relaxed state and a rigid state, the orthotic device including a base and an appendage housing coupled to the base, the appendage housing including at least one activation component responsive to an activation signal output by a controller in communication with the fastener installation tool, wherein the base is pivotably couplable to a handle of the fastener installation tool;
outputting, by the controller coupled in communication with the fastener installation tool, the activation signal, based on operation of the fastener installation tool; and
changing, by the at least one activation component, the orthotic device from the relaxed state to the rigid state in response to the activation signal output by the controller.

19. The method of claim 18, wherein outputting the activation signal, based on operation of the fastener installation tool, comprises outputting, by the controller, the activation signal in response to detecting activation of the fastener installation tool.

20. The method of claim 18, wherein the at least one activation component includes at least one bladder configured to be worn around the appendage of the user of the fastener installation tool, wherein changing the orthotic device from the relaxed state to the rigid state comprises inflating the at least one bladder in response to the activation signal output from the controller.

* * * * *